US011401560B2

(12) United States Patent
Xu et al.

(10) Patent No.: US 11,401,560 B2
(45) Date of Patent: Aug. 2, 2022

(54) SET OF GENES FOR BLADDER CANCER DETECTION AND USE THEREOF

(71) Applicant: HANGZHOU CANHELP GENOMICS TECHNOLOGY CO. LTD., Hangzhou (CN)

(72) Inventors: Qinghua Xu, Hangzhou (CN); Dingwei Ye, Hangzhou (CN); Qifeng Wang, Hangzhou (CN); Chengshu Chen, Hangzhou (CN); Jinying Chen, Hangzhou (CN); Yifeng Sun, Hangzhou (CN); Wanli Ren, Hangzhou (CN); Hongying Wang, Hangzhou (CN); Yiwang Wu, Hangzhou (CN); Tao Huo, Hangzhou (CN)

(73) Assignee: HANGZHOU CANHELP GENOMICS TECHNOLOGY CO. LTD., Hangzhou (CN)

( * ) Notice: Subject to any disclaimer, the term of this patent is extended or adjusted under 35 U.S.C. 154(b) by 0 days.

(21) Appl. No.: 17/267,810

(22) PCT Filed: Jan. 17, 2019

(86) PCT No.: PCT/CN2019/072196
§ 371 (c)(1),
(2) Date: Feb. 11, 2021

(87) PCT Pub. No.: WO2020/034583
PCT Pub. Date: Feb. 20, 2020

(65) Prior Publication Data
US 2021/0180140 A1 Jun. 17, 2021

(30) Foreign Application Priority Data

Aug. 16, 2018 (CN) .......................... 201810933616.2

(51) Int. Cl.
*C12P 19/34* (2006.01)
*C12Q 1/6886* (2018.01)
*G16B 50/00* (2019.01)

(52) U.S. Cl.
CPC ........... *C12Q 1/6886* (2013.01); *G16B 50/00* (2019.02); *C12Q 2600/158* (2013.01)

(58) Field of Classification Search
CPC .................................................. C12Q 1/6886
See application file for complete search history.

(56) References Cited

U.S. PATENT DOCUMENTS

| 2016/0017433 A1* | 1/2016 | Alcaraz Asensio .... A61B 18/12 506/9 |
| 2016/0146818 A1* | 5/2016 | Goodison ............ C12Q 1/6886 506/9 |
| 2017/0002420 A1* | 1/2017 | Guilford .......... G01N 33/57407 |

FOREIGN PATENT DOCUMENTS

| CN | 101730848 A | 6/2010 |
| CN | 104450893 A | 3/2015 |
| CN | 105087568 A | 11/2015 |
| CN | 105229169 A | 1/2016 |
| CN | 107326066 A | 11/2017 |
| CN | 107723368 A | 2/2018 |
| WO | 2014118334 A1 | 8/2014 |

OTHER PUBLICATIONS

Wanqing Chen, et al., Cancer Statistics in China, CA Cancer J Clin, 2015, pp. 115-132, vol. 66 No. 2.
V. Pansadoro, et al. Bacillus Calmette-Guerin in the Treatment of Stage T1 Grade 3 Transitional Cell Carcinoma of the Bladder: Long-term Results. J Urol, 1995, pp. 2054-2058, 154(6).
F. Millán-Rodríguez, et al. Primary superficial bladder cancer risk groups according to progression, mortality, and recurrence, The Journal of Urology, 2000, pp. 680-684, 164(3).
Sambrook et al., Molecular Cloning: Laboratory Manual, 1989, New York: Cold Spring Harbor Laboratory Press.
Virginia Urquidi, et al. A Candidate Molecular Biomarker Panel for the Detection of Bladder Cancer, Cancer Epidemiol Biomarkers Prev, 2012, pp. 2149-2158, 21(12).
Cai-Shu Liu, et al., Present Situation and Prospect of Urinary Biomarkers For Bladder Cancer, Advances in Physiological Sciences, 2015, pp. 255-258, vol. 46 No.4.
Gunhee Lee, et al., Classification of Genes Based on Age-Related Differential Expression in Breast Cancer, Genomics Informatics, 2017, pp. 156-161, vol. 15 No. 4.
Qin-Rong Ping, et al. The Clinical Value of Early Diagnostic Methods of Bladder Cancer, Medicine and Philosophy, 2015, pp. 66-69, vol. 36 No. 3B.

\* cited by examiner

*Primary Examiner* — Kenneth R Horlick
(74) *Attorney, Agent, or Firm* — Bayramoglu Law Offices LLC

(57) ABSTRACT

Disclosed are a set of genes for bladder cancer detection and their use. The set of genes includes the following 32 genes: CA9 gene, CDK1 gene, CTSE gene, DMBT1 gene, ERBB2 gene, HOXA13 gene, IGF2 gene, CXCR2 gene, MAGEA3 gene, MDK gene, MMP1 gene, MMP12 gene, RBP2 gene, CCL18 gene, SNAI2 gene, VEGFA gene, MFAP5 gene, SGK2 gene, WFDC2 gene, POSTN gene, NPFFR2 gene, ANXA10 gene, CTAG2 gene, ZDHHC2 gene, KRT20 gene, PPP1R14D gene, FGD3 gene, AHNAK2 gene, SEMA3D gene, ZNF707 gene, LOC100652931 gene, and LINC00565 gene. After clinical validation, the kit provided by the present invention is used to detect bladder cancer with a high accuracy rate and objective interpretation of results. Meanwhile, as a non-invasive detection, the compliance of patients is greatly improved comparing with the existing cystoscopy, which has an important clinical significance for the early detection and postoperative monitoring of bladder cancer.

15 Claims, 1 Drawing Sheet
Specification includes a Sequence Listing.

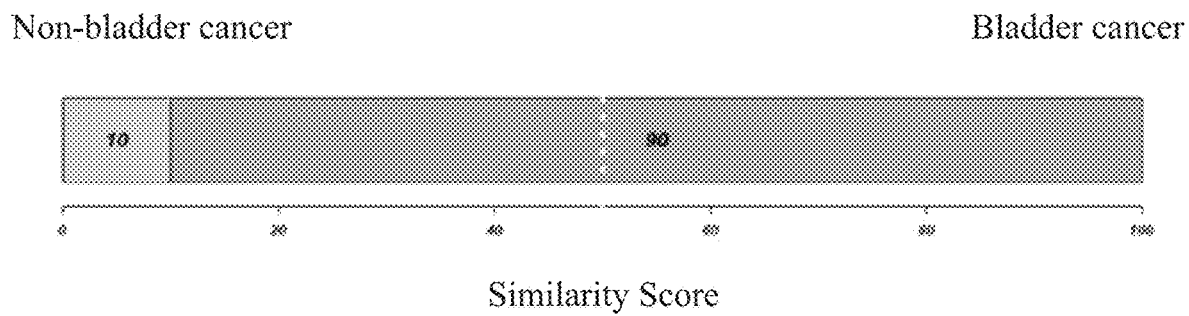

SET OF GENES FOR BLADDER CANCER DETECTION AND USE THEREOF

CROSS REFERENCE TO THE RELATED APPLICATIONS

This application is the national phase entry of International Application No. PCT/CN2019/072196, filed on Jan. 17, 2019, which is based upon and claims priority to Chinese Patent Application No. 201810933616.2, filed on Aug. 16, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHHY013-SEQUENCE LISTING.txt and is 22,524 bytes in size.

TECHNICAL FIELD

The present invention relates to the field of cancer diagnosis and molecular biology, as well as the clinical application of the diagnostic techniques. Specifically, the present invention relates to a set of genes for bladder cancer detection (including diagnosis, prognosis, and monitoring) and use thereof, which is by way of detecting the expression of specific genes from desquamated cells in the urine to identify whether the diagnostic subjects suffer bladder cancer. Also, the present invention relates to a kit for bladder cancer detection.

BACKGROUND

Bladder cancer is a malignant tumor occurring on the bladder mucosa, which is the most common malignant tumor of the urinary system and is also one of the top ten common tumors. Bladder cancer occupies the first place in the incidence of genitourinary tumors in China and is the second most common tumor only after prostate cancer in the West. China Cancer Statistics (Chen W, Zheng R, Baade P D, et al. Cancer statistics in China, 2015[J]. Ca Cancer J Clin, 2016, 66(2):115-132) showed that the number of new cases in China reached about 80,500 in 2015, males are 3.3 times more likely than females. The death toll is estimated at more than 32,900, with a mortality rate of more than 40%, 3.2 times higher for males than females. Currently, approximately 80% of bladder tumors are non-invasive papilloma (pTa or pT1), with a 5-year survival rate of approximately 90% and a 10-year survival rate of approximately 80% (Pansadoro V, Emiliozzi P, Defidio L, et al. Bacillus Calmette-Guerin in the Treatment of Stage T1 Grade 3 Transitional Cell Carcinoma of the Bladder: Long-term Results[J]. J Urol, 1995, 154(6):2054-2058.) The remaining patients with muscle-invasive tumors during diagnosis tend to have a poor prognosis. Therefore, early diagnosis can significantly improve the survival time and the life quality of patients.

Although the muscle-invasive diseases require radical surgical treatment, non-muscle invasive tumors, with or without bladder perfusion therapy, can be treated more conservatively by transurethral resection of the tumor. However, more than 70% of patients with early-stage diseases tend to relapse within the first two years after diagnosis, making bladder cancer one of the most common cancers. If left untreated, these initially non-invasive lesions may evolve into muscle-invasive lesions (Millánrodríguez F, Chéchiletoniolo G, Salvadorbayarri J, et al. Primary superficial bladder cancer risk groups according to progression, mortality, and recurrence. [J]. Journal of Urology, 2000, 164(3):680-684.) The recurrence of bladder cancer means that patients need to be strictly monitored at least once a year. For life quality and positive clinical outcomes, the timely detection of the recurrence is as important as early diagnosis.

Currently, the main detection method is cystoscopy combined with the Voided Urine Cytology (VUC). Cystoscopy is an invasive method that causes severe discomfort, is costly, and can lead to infection and trauma. This makes some early-phase patients have resistant to cystoscopy, which often delays the diagnosis and timely treatment of the disease. Cytology is an alternative method of non-invasive screening for bladder cancer. However, the interpretation of the results is highly dependent on the observer; consequently, the results are more subjective, especially in low-grade tumors. Therefore, alternative methods for the non-invasive diagnosis of bladder cancer that allow objective diagnosis with high sensitivity and specificity are still needed to be developed.

Tumors are genomic diseases. Genomic changes play an essential role in tumor genesis and development. In 1999, the National Cancer Institute of the United States published a research project proposal for the first time to provide more information for tumor classification through comprehensive molecular analysis techniques. Further tumor classification is transformed from the traditional morphology to the molecular feature-based "molecular classifying." In recent years with the rapid development of molecular biology and bioinformatics technology, researchers have used biochip and high-throughput sequencing technology to simultaneously measure the expression level of thousands of genes in tumor tissue, from which genes relating to tumor subgroups and specific expression patterns were found. Domestic and foreign-related studies have reported that gene expression profile analysis can assist in elucidating the nature of the tumor and accurately classify tumors at a molecular level. For example, Varadhachary and Talantov, et al, identified ten tissue-specific genes to identify lung cancer, breast cancer, colon cancer, ovarian cancer, pancreatic cancer, and prostate cancer with an accuracy rate of 78%. Ma et al. detected the expression of 92 genes in tumor tissue and identified 32 tumor types with an accuracy rate of 87%. Rosenfeld et al. reported a 48 microRNAs assay that identified 22 tumor types with an accuracy rate of 89%. In China, the inventors first disclosed a set of genes for tumor molecular classifying and use thereof in 2015 (patent application number: 201510550924.3). This set of genes can be used to differentiate 22 types of cancer. Among the ten most common tumors in male and female of China, the classifying accuracy rate of the 96-gene model reached 95.5% and 93.2%, respectively. Although this set of genes have excellent performance for differential diagnosis of bladder cancer, with a sensitivity of 87.5% and a specificity of 100%, it is mainly used in paraffin tissue specimens.

International patent application WO2014/118334 describes a non-invasive in vitro method for diagnosing bladder cancer based on the expression pattern of specific genes in the urine samples. Although the method has shown high sensitivity (78.7%) and specificity (93.2%) in validation studies in western populations, further experiments are needed to confirm whether it is still applicable to Chinese populations. Only a very small amount of desquamated cells of the tumor were contained in the urine; therefore, how to extract a sufficient amount of RNA from the tiny amount of desquamated cells of the tumor to accurately detect the expression abundance of bladder cancer-related genes is difficult in the current urine bladder oncogene detection. The existing detection methods mainly have the following deficiencies:

1. The existing method uses Trizol solvent to purify and extract RNA from desquamated cells in the urine. In the experimental process, the supernatant needs to be repeatedly eluted and removed, and the steps are too complicated and difficult to control, further easy to cause RNA loss and ultimately affect the yield and purity of RNA. For example, international patent application WO2014/118334 describes that the Trizol (Invitrogen, Carlsbad, Calif., USA) extraction method was used for the treatment of the urine samples in examples. Consequently, out of 790 subjects, 256 (31%) were excluded due to substandard quality. The valid samples were 534, and the test success rate was only 69%.

2. In order to detect the expression abundance of bladder cancer-specific genes in trace amounts of RNA, it is required that the detected genes have high specificity for bladder cancer. When the specificity of gene combination is not high enough, the pre-amplification is often needed after reverse transcription to enrich a certain amount of the detected substances to ensure the implementation of the subsequent quantitative process. After finishing the pre-amplifying, the PCR reaction tube should be opened during the experiment, and the specific probe primers of the target gene should be added again. The opening process is likely to cause the diffusion of PCR aerosols, further lead to laboratory contamination. In clinical laboratories dealing with large sample size and heavy detection task, the application of pre-amplification technology has great risks and challenges.

3. The experimental procedures of the existing detection methods include: the pretreatment of a urine sample and RNA extraction (3 hours), the reverse transcription (2.5 hours), the pre-amplification (2 hours), the amplification (2 hours), and the detection analysis (0.5 hours). The entire experiment is conservatively estimated to have taken over 10 hours. In clinical practice, one sample's detection takes two business days, so that the clinical application faces significant challenges.

SUMMARY

A technical problem to be solved in the present invention is to provide a set of genes for bladder cancer detection, to establish a statistical analysis model of bladder cancer, further to assist patients in achieving individualized treatment. It has the advantages of good specificity, high success rate of detection, simple and rapid operation, and can better meet the urgent clinical needs for non-invasive detection of bladder cancer.

A second technical problem to be solved in the present invention is to provide the use of a set of genes for bladder cancer detection.

A third technical problem to be solved in the present invention is to provide a kit for bladder cancer detection and use thereof.

A fourth technical problem to be solved in the present invention is to provide the use of a set of genes for bladder cancer detection for the preparation of a gene chip for the diagnosis, prognosis, or monitoring of bladder cancer.

To resolve the above technical problems, the present invention adopts the following technical solutions:

In one aspect, the present invention provides a set of genes for bladder cancer detection comprising the following 32 genes: CA9 gene, CDK1 gene, CTSE gene, DMBT1 gene, ERBB2 gene, HOXA13 gene, IGF2 gene, CXCR2 gene, MAGEA3 gene, MDK gene, MMP1 gene, MMP12 gene, RBP2 gene, CCL18 gene, SNAI2 gene, VEGFA gene, MFAP5 gene, SGK2 gene, WFDC2 gene, POSTN gene, NPFFR2 gene, ANXA10 gene, CTAG2 gene, ZDHHC2 gene, KRT20 gene, PPP1R14D gene, FGD3 gene, AHNAK2 gene, SEMA3D gene, ZNF707 gene, LOC100652931 gene, and LINC00565 gene.

The Gene ID of CA9 used herein is 768, and the Accession No. in GenBank database is NM_001216.2.

The Gene ID of CDK1 used herein is 983, and the Accession No. in GenBank database is NM_001786.4.

The Gene ID of CTSE used herein is 1510, and the Accession No. in GenBank database is NM_001317331.1.

The Gene ID of DMBT1 used herein is 1755, an e Accession No. in GenBank database is NM_001320644.1.

The Gene ID of ERBB2 used herein is 2064, and the Accession No. in GenBank database is NM_001289937.1.

The Gene ID of HOXA13 used herein is 3209, and the Accession No. in GenBank database is NM_000522.4.

The Gene ID of IGF2 used herein is 3481, and the Accession No. in GenBank database is NM_000612.

The Gene ID of CXCR2 used herein is 3579, and the Accession No. in GenBank database is NM_001168298.1.

The Gene ID of MAGEA3 used herein is 4102, and the Accession No. in GenBank database is NM_005362.3.

The Gene ID of MDK used herein is 4192, and the Accession No. in GenBank database is NM_001130143.1.

The Gene ID of MMP1 used herein is 4312, and the Accession No. in GenBank database is NM_001145938.1.

The Gene ID of MMP12 used herein is 4321, and the Accession No. in GenBank database is NM_002426.5.

The Gene ID of RBP2 used herein is 5948, and the Accession No. in GenBank database is NM_004164.2.

The Gene ID of CCL18 used herein is 6362, and the Accession No. in GenBank database is NM_002988.3.

The Gene ID of SNAI2 used herein is 6591, and the Accession No. in GenBank database is NM_003068.4.

The Gene ID of VEGFA used herein is 7422, and the Accession No. in GenBank database is NM_001025366.2.

The Gene ID of MFAP5 used herein is 8076, and the Accession No. in GenBank database is NM_001297709.1.

The Gene ID of SGK2 used herein is 10110, and the Accession No. in GenBank database is NM_001199264.1.

The Gene ID of WFDC2 used herein is 10406, and the Accession No. in GenBank database is NM_006103.3.

The Gene ID of POSTN used herein is 10631, and the Accession No. in GenBank database is NM_001135934.1.

The Gene ID of NPFFR2 used herein is 10886, and the Accession No. in GenBank database is NM_001144756.1.

The Gene ID of ANXA10 used herein is 11199, and the Accession No. in GenBank database is NM_007193.4.

The Gene ID of CTAG2 used herein is 30848, and the Accession No. in GenBank database is NM_020994.4.

The Gene ID of ZDHHC2 used herein is 51201, and the Accession No. in GenBank database is NM_001362988.1.

The Gene ID of KRT20 used herein is 54474, and the Accession No. in GenBank database is NM_019010.2.

The Gene ID of PPP1R14D used herein is 54866, and the Accession No. in GenBank database is XM_017022372.1.

The Gene ID of FGD3 used herein is 89846, and the Accession No. in GenBank database is NM_001083536.1.

The Gene ID of AHNAK2 used herein is 113146, and the Accession No. in GenBank database is NM_001350929.1.

The Gene ID of SEMA3D used herein is 223117, and the Accession No. in GenBank database is NM_152754.2.

The Gene ID of ZNF707 used herein is 286075, and the Accession No. in GenBank database is NM_001100598.1.

The Gene ID of LOC100652931 used herein is 100652931, and the Accession No. in GenBank database is NR_104151.1.

The Gene ID of LINC00565 used herein is 100861555, and the Accession No. in GenBank database is NR_047495.1.

The detection result of bladder cancer is bladder cancer positive or bladder cancer negative; the sample for bladder cancer detection is a urine sample.

The pretreatment method of the urine sample consists of the following steps: first, centrifuging the desquamated cells in the urine, and then extracting the total RNA by purification column extraction method using the purification column as the liquid elution medium.

The genes were screened by the following method: selecting the gene combinations with high specificity to bladder cancer by using the analysis technique of "big data and algorithm drive"; firstly, building bladder cancer gene expression profile database, containing over 20,000 genes known to mankind, 92 samples, over 2 million data points; correlating more than 20,000 human gene expression data in each sample with the clinical data of the samples; and then screening specific bladder cancer genes through a statistical analysis method T-test, namely analyzing the relevance of each gene to bladder cancer, and extracting the genes with the highest correlation as signature genes, eventually obtaining 32 genes for constructing the classifying model; establishing a statistical analysis model for bladder cancer detection by using Support Vector Machine, for each sample to be tested, the model calculated the Similarity Score between the gene expression pattern of the sample and bladder cancer in the database and identified whether the samples had bladder cancer according to the principle of the highest Similarity Score.

The present invention establishes a gene-marker combination model through the combined application of gene detection, marker combination, and data mining algorithm, and uses the polygene prediction model to differentially diagnose whether the subjects suffer bladder cancer. It mainly includes the following steps:

(1) Collecting the clinical diagnostic data and gene expression data of bladder cancer and constructing a gene expression profile database containing 20,500 known genes and 92 samples of bladder cancer;

(2) Conducting a statistical analysis of the gene expression patterns and screening out 32 genes closely related to bladder cancer: CA9 gene, CDK1 gene, CTSE gene, DMBT1 gene, ERBB2 gene, HOXA13 gene, IGF2 gene, CXCR2 gene, MAGEA3 gene, MDK gene, MMP1 gene, MMP12 gene, RBP2 gene, CCL18 gene, SNAI2 gene, VEGFA gene, MFAP5 gene, SGK2 gene, WFDC2 gene, POSTN gene, NPFFR2 gene, ANXA10 gene, CTAG2 gene, ZDHHC2 gene, KRT20 gene, PPP1R14D gene, FGD3 gene, AHNAK2 gene, SEMA3D gene, ZNF707 gene, LOC100652931 gene, and LINC00565 gene, respectively;

(3) Calculating the expression patterns of the above 32 genes, evaluating bladder cancer by the statistical analysis model, and calculating the Similarity Score between biological samples and bladder cancer. According to the rule of the highest Similarity Score, identifying whether the diagnosed objects suffer bladder cancer.

The present invention provides a detection method for identifying bladder cancer, comprising the following steps:

(1) Contacting the biological samples from patients, with bladder cancer or with bladder cancer risk, with the biomarkers that include the 32 genes as mentioned above; the biological samples are in-vitro biological samples from the subjects, which can be a sample of bladder fluid, such as urine, bladder washing, etc.

On this basis, conducting a further identification of bladder cancer:

(2) Detecting the expression patterns and the level of 32 genes in biological samples and identifying whether the biological samples are of bladder cancer based on the expression level of 32 genes; calculating the Similarity Score between biological samples and bladder cancer by using the data analysis method. According to the rule of the highest Similarity Score, identifying whether the diagnostic subjects suffer bladder cancer. The detection involves the preparation of RNA from the samples; the RNA was used for polymerase chain reaction (PCR); the PCR is a reverse transcription PCR (RT-PCR), optionally with real-time RT-PCR or the gene chip or high-throughput sequencing technology.

In a second aspect, the present invention provides the use of a set of genes for bladder cancer detection for the preparation of a kit for bladder cancer detection.

In a third aspect, the present invention provides a kit for bladder cancer detection; the kit comprises the following biomarkers; the biomarkers are selected from any one or more of the genes for bladder cancer detection.

As a preferred technical solution, the biomarkers are nucleic acids, oligonucleotide chains, or PCR primer sets.

As a preferred technical solution, the PCR primer sets comprise:

CA9 gene: the forward primer is as set forth in SEQ ID NO: 1, and the reverse primer is as set forth in SEQ ID NO: 2;

CDK1 gene: the forward primer is as set forth in SEQ ID NO: 3, and the reverse primer is as set forth in SEQ ID NO: 4;

CTSE gene: the forward primer is as set forth in SEQ ID NO: 5, and the reverse primer is as set forth in SEQ ID NO: 6;

DMBT1 gene: the forward primer is as set forth in SEQ ID NO: 7, and the reverse primer is as set forth in SEQ ID NO: 8;

ERBB2 gene: the forward primer is as set forth in SEQ ID NO: 9, and the reverse primer is as set forth in SEQ ID NO: 10;

HOXA13 gene: the forward primer is as set forth in SEQ ID NO: 11, and the reverse primer is as set forth in SEQ ID NO: 12;

IGF2 gene: the forward primer is as set forth in SEQ ID NO: 13, and the reverse primer is as set forth in SEQ ID NO: 14;

CXCR2 gene: the forward primer is as set forth in SEQ ID NO: 15, and the reverse primer is as set forth in SEQ ID NO: 16;

MAGEA3 gene: the forward primer is as set forth in SEQ ID NO: 17, and the reverse primer is as set forth in SEQ ID NO: 18;

MDK gene: the forward primer is as set forth in SEQ ID NO: 19, and the reverse primer is as set forth in SEQ ID NO: 20;

MMP1 gene: the forward primer is as set forth in SEQ ID NO: 21, and the reverse primer is as set forth in SEQ ID NO: 22;

MMP12 gene: the forward primer is as set forth in SEQ ID NO: 23, and the reverse primer is as set forth in SEQ ID No. 24;

RBP2 gene: the forward primer is as set forth in SEQ ID NO: 25, and the reverse primer is as set forth in SEQ ID NO: 26;

CCL18 gene: the forward primer is as set forth in SEQ ID NO: 27, and the reverse primer is as set forth in SEQ ID NO: 28;

SNAI2 gene: the forward primer is as set forth in SEQ ID NO: 29, and the reverse primer is as set forth in SEQ ID NO: 30;

VEGFA gene: the forward primer is as set forth in SEQ ID NO: 31, and the reverse primer is as set forth in SEQ ID NO: 32;

MFAP5 gene: the forward primer is as set forth in SEQ ID NO: 33, and the reverse primer is as set forth in SEQ ID NO: 34;

SGK2 gene: the forward primer is as set forth in SEQ ID NO: 35, and the reverse primer is as set forth in SEQ ID NO: 36;

WFDC2 gene: the forward primer is as set forth in SEQ ID NO: 37, and the reverse primer is as set forth in SEQ ID NO: 38;

POSTN gene: the forward primer is as set forth in SEQ ID NO: 39, and the reverse primer is as set forth in SEQ ID NO: 40;

NPFFR2 gene: the forward primer is as set forth in SEQ ID NO: 41, and the reverse primer is as set forth in SEQ ID NO: 42;

ANXA10 gene: the forward primer is as set forth in SEQ ID NO: 43, and the reverse primer is as set forth in SEQ ID NO: 44;

CTAG2 gene: the forward primer is as set forth in SEQ ID NO: 45, and the reverse primer is as set forth in SEQ ID NO: 46;

ZDHHC2 gene: the forward primer is as set forth in SEQ ID NO: 17, and the reverse primer is as set forth in SEQ ID NO: 48;

KRT20 gene: the forward primer is as set forth in SEQ ID NO: 49, and the reverse primer is as set forth in SEQ ID NO: 50;

PPP1R14D gene: the forward primer is as set forth in SEQ ID NO: 51, and the reverse primer is as set forth in SEQ ID NO: 52;

FGD3 gene: the forward primer is as set forth in SEQ ID NO: 53, and the reverse primer is as set forth in SEQ ID NO: 54;

AHNAK2 gene: the forward primer is as set forth in SEQ ID NO: 55, and the reverse primer is as set forth in SEQ ID NO: 56;

SEMA3D gene: the forward primer is as set forth in SEQ ID NO: 57, and the reverse primer is as set forth in SEQ ID NO: 58;

ZNF707 gene: the forward primer is as set forth in SEQ ID NO: 59, and the reverse primer is as set forth in SEQ ID NO: 60;

LOC100652931 gene: the forward primer is as set forth in SEQ ID NO: 61, and the reverse primer is as set forth in SEQ ID NO: 62;

LINC00565 gene: the forward primer is as set forth in SEQ ID NO: 63, and the reverse primer is as set forth in SEQ ID NO: 64.

The use method of the above-mentioned kit includes the following steps:

(1) Contacting the biological samples with the biomarkers;

(2) Determining the expression level of the markers in the biological samples;

(3) Detecting the gene expression patterns in biological samples and comparing with the gene expression profile database of bladder cancer.

The expression of the kit can be detected by real-time quantitative reverse transcription polymerase chain reaction (RT-PCR), or by the gene chips, or by high-throughput sequencing techniques.

The expression level detected by the kit is the mRNA expression level.

Only as a supplementary example of the above-mentioned in the present invention, for the desquamated cells in the urine from the diagnostic subjects, the real-time quantitative reverse transcriptional polymerase chain reaction (RT-PCR) is used to identify bladder cancer, which includes the following steps:

(1) Obtaining the desquamated cells in the urine from the diagnostic subjects;

(2) Detecting the expression of 32 genes in the sample through real-time quantitative reverse transcription polymerase chain reaction;

(3) Detecting the expression patterns of 32 genes in the sample and comparing with the gene expression profile data of bladder cancer to identify whether the biological sample is of bladder cancer.

In a fourth aspect, the present invention provides the use of the kit for the preparation of a formulation for the diagnosis, prognosis, or monitoring of bladder cancer.

In a fifth aspect, the present invention provides the use of a set of genes for the preparation of a gene chip for the diagnosis, prognosis, or monitoring of bladder cancer, wherein the gene chip comprises a solid phase carrier and a probe, wherein the probe is hybridized with the 32 gene sequences to be tested and/or their complementary sequences, wherein the 32 genes to be tested are CA9 gene, CDK1 gene, CTSE gene, DMBT1 gene, ERBB2 gene, HOXA13 gene, IGF2 gene, CXCR2 gene, MAGEA3 gene, MDK gene, MMP1 gene, MMP12 gene, RBP2 gene, CCL18 gene, SNAI2 gene, VEGFA gene, MFAP5 gene, SGK2 gene, WFDC2 gene, POSTN gene, NPFFR2 gene, ANXA10 gene, CTAG2 gene, ZDHHC2 gene, KRT20 gene, PPP1R14D gene, FGD3 gene, AHNAK2 gene, SEMA3D gene, ZNF707 gene, LOC100652931 gene, and LINC00565 gene; wherein the probe is as set forth in SEQ ID NO: 65-SEQ ID NO: 96, respectively.

The present invention establishes a statistical analysis model to identify whether the urine sample is of bladder cancer by detecting 32 bladder cancer-related genes in the urine sample. To assist doctors in clinical decision-making and achieve precise medicine to improve patients' survival rate with bladder cancer. After clinical validation, the kit provided by the present invention is used to detect bladder cancer with high accuracy rate and objective interpretation of results. Meanwhile, as a non-invasive detection, patients' compliance is greatly improved compared with the existing cystoscopy, which has an important clinical significance for the early discovery and postoperative monitoring of bladder cancer.

Comparing with the prior art (International patent application WO2014/118334), the beneficial effects of the present invention are as follows:

1. The present invention improved the extraction and purification method of RNA in the urine and innovatively used the purification column as the medium of liquid elution, thus eliminated the step of repeated elution. While the yield and purity of RNA were significantly improved, the experimental process was greatly simplified, and the success rate of detection was increased from 69% to 93%. Therefore, the urine sample pretreatment method adopted by the present invention has the advantages of high RNA yield, high detection success rate, and quick and simple operation.

2. The present invention selects the gene combinations with high specificity to bladder cancer using the analysis technique of "big data and algorithm drive." The inventors build the gene expression profile database of bladder cancer containing over 20,000 genes known to mankind, 92 samples, over 2 million data points. Correlate more than 20,000 human gene expression data in each sample with clinical data of the samples, and then screen the specific bladder cancer genes through the statistical analysis method T-test, namely analyze the relevance of each gene to bladder cancer, and extract the highest correlation genes as signature genes. Eventually, the inventors obtain 32 genes for constructing the classifying model. According to the general principles of machine learning, the 32 gene combinations are the most closely related to the occurrence of bladder cancer among more than 20,000 genes known to humans; therefore, they have a good specificity. Due to the good specificity of the 32 gene combinations provided by the present invention, the expression of bladder cancer-specific genes can be detected by very small amount of tumor cells in the urine. The detection can be completed through the classic two-step PCR (reverse transcription+amplification), avoiding the problems of laboratory contamination caused by pre-amplification technology and achieving the technical effects that cannot be expected by the existing methods.

3. By improving the sample pretreatment method, the specificity of the detected gene is improved, unnecessary pre-amplification steps are removed, the time required for the experiment is shortened to 5 hours, which is only half of that of the existing methods, and the detection efficiency is significantly improved. The detection can be completed on the same day; therefore, it is more suitable for clinical use.

To sum up, the inventors, through the creative work, provide a set of gene combinations for bladder cancer detection and the detection kit thereof. The present invention is of the advantages of good specificity, high success rate of detection, quick and simple operation, which can better meet the urgent clinical needs for non-invasive detection for bladder cancer.

BRIEF DESCRIPTION OF THE DRAWINGS

FIGURE is a schematic diagram of bladder cancer detection results of 32-gene model in Example 3 of the present invention.

DETAILED DESCRIPTION OF THE EMBODIMENTS

The present invention will be further described by reference to the following examples, which are illustrative only and are not intended to limit the present invention. The experimental methods without specific conditions in examples are conducted based on the conditions recommended by the manufacturer of the kit or based on the conventional experimental conditions, such as described by Sambrook et al., Molecular Cloning: Laboratory Manual (New York: Cold Spring Harbor Laboratory Press, 1989). Unless otherwise defined, all professional and scientific terms used herein shall have the same meanings familiar to skilled personnel in the field. In addition, any methods and materials similar to or equal to the recorded content may be applied to the present invention. The better examples and materials described in the present invention are only for demonstration purposes.

Example 1

Collecting and processing of training set samples:
The present invention analyzed clinical data of 92 urine samples, from 52 patients with bladder cancer and 40 patients with other urinary system diseases other than bladder cancer, and 20,500 gene expression abundance data, then constructed the gene expression database of bladder cancer.

Screening of 32 specific genes:
According to the test value of gene expression abundance, 32 genes closely related to bladder cancer were screened from 20,250 genes through the statistical analysis method T-test. These genes were differentially expressed in bladder cancer; therefore, they are of statistically significant: association as shown in Table 1.

TABLE 1

32-gene set

| Genes | Gene ID | Description | T-Test P Value |
|---|---|---|---|
| CA9 | 768 | carbonic anhydrase IX | <0.001 |
| CDK1 | 983 | cyclin-dependent kinase 1 | <0.001 |
| CTSE | 1510 | cathepsin E | <0.001 |
| DMBT1 | 1755 | deleted in malignant brain tumors 1 | <0.001 |
| ERBB2 | 2064 | erb-b2 receptor tyrosine kinase 2 | <0.001 |
| HOXA13 | 3209 | homeobox A13 | <0.001 |
| IGF2 | 3481 | insulin-like growth factor 2 | <0.001 |
| CXCR2 | 3579 | chemokine (C-X-C motif) receptor 2 | <0.001 |
| MAGEA3 | 4102 | melanoma antigen family A3 | <0.001 |
| MDK | 4192 | midkine (neurite growth-promoting factor 2) | <0.001 |
| MMP1 | 4312 | matrix metallopeptidase 1 (interstitial collagenase) | <0.001 |
| MMP12 | 4321 | matrix metallopeptidase 12 (macrophage elastase) | <0.001 |
| RBP2 | 5948 | retinol binding protein 2, cellular | <0.001 |
| CCL18 | 6362 | chemokine (C-C motif) ligand 18 (pulmonary and activation-regulated) | <0.001 |
| SNAI2 | 6591 | snail family zinc finger 2 | <0.001 |
| VEGFA | 7422 | vascular endothelial growth factor A | <0.001 |
| MFAP5 | 8076 | microfibrillar associated protein 5 | <0.001 |
| SGK2 | 10110 | serum/glucocorticoid regulated kinase 2 | <0.001 |
| WFDC2 | 10406 | WAP four-disulfide core domain 2 | <0.001 |

TABLE 1-continued 32-gene set

| Genes | Gene ID | Description | T-Test P Value |
|---|---|---|---|
| POSTN | 10631 | periostin, osteoblast specific factor | <0.001 |
| NPFFR2 | 10886 | neuropeptide FF receptor 2 | <0.001 |
| ANXA10 | 11199 | annexin A10 | <0.001 |
| CTAG2 | 30848 | cancer/testis antigen 2 | <0.001 |
| ZDHHC2 | 51201 | zinc finger, DHHC-type containing 2 | <0.001 |
| KRT20 | 54474 | keratin 20, type I | <0.001 |
| PPP1R14D | 54866 | protein phosphatase 1, regulatory (inhibitor) subunit 14D | <0.001 |
| FGD3 | 89846 | FYVE, RhoGEF and PH domain containing 3 | <0.001 |
| AHNAK2 | 113146 | AHNAK nucleoprotein 2 | <0.001 |
| SEMA3D | 223117 | sema domain, immunoglobulin domain (Ig), short basic domain, secreted, (semaphorin) 3D | <0.001 |
| ZNF707 | 286075 | zinc finger protein 707 | <0.001 |
| LOC100652931 | 100652931 | RNA binding motif protein, Y-linked, family 1, member A1 pseudogene | <0.001 |
| LINC00565 | 100861555 | long intergenic non-protein coding RNA 565 | <0.001 |

Construction of 32-Gene Statistical Analysis Model:

Based on the expression patterns of 32 signature genes in samples of bladder cancer and non-bladder cancer, the inventors established a statistical analysis model for bladder cancer detection by using Support Vector Machine. For each sample to be tested, the model calculated the Similarity Score between the gene expression pattern of the sample and bladder cancer in the database and identified whether the samples had bladder cancer according to the principle of the highest Similarity Score. Since its invention in 1992, the Support Vector Machine has been widely used to solve a variety of recognition problems, including financial data analysis, speech identification, and biological data analysis. The technicians in this field can use Support Vector Machine with open source, free analysis software, such as R, Rapid-Miner, and WEKA. Not limited to Support Vector Machine, other informed data mining methods can be used, such as Weighted Voting, k-Nearest Neighbors, Random Forest, Correlation Coefficients, etc.

Example 2

In the Example, the inventors analyzed the high-throughput sequencing data of 107 urine samples, including 63 samples with bladder cancer and 44 samples with non-bladder cancer. After identifying each sample by 32-gene statistical analysis model and comparing it with the clinical diagnosis results, the accuracy rate was 91.6%, the sensitivity is 92.1%, and the specificity is 90.9%, as shown in Table 2.

Example 3

In the present example, the inventors collected 114 urine samples, including 80 samples with bladder cancer and 34 samples with non-bladder cancer. The researchers first centrifuged the desquamated cells in the urine, and then extracted total RNA by a purified column extraction method instead of the traditional Trizol method. Among them, 8 samples were excluded due to substandard RNA quality, with a rejection rate of 7%. Finally, 106 samples were included in the study, including 74 samples with bladder cancer and 32 samples with non-bladder cancer. The cDNA was obtained by reverse transcription after extracting and purifying RNA, and then was detected the gene expression level of the desquamated cells from the urine through a real-time quantitative polymerase chain reaction of 32-gene model. The similarity Score between this sample and bladder cancer was calculated by the analysis model.

International patent application WO2014/118334 describes that the TRIzol (Invitrogen, Carlsbad, Calif., USA) extraction method is used in examples for the treatment of 790 urine samples, 256 (31%) were excluded due to substandard quality; the remaining valid samples were 534, and the test success rate was only 69%. The inventor innovatively improved the extraction method based on the traditional Trizol extraction method, namely the purification column extraction method was used to significantly improve the yield and purity of RNA, and the success rate of detection was increased to 93%.

Each sample type was identified by the 32-gene statistical analysis model and compared with the clinical diagnosis results, the accuracy rate was 93.4%, the sensitivity was 91.9%, and the specificity was 96.9%, as shown in Table 3.

TABLE 2

Identification results of 32-gene model in 107 samples from validation set

| Validation Set 1 | | Identification results of 32-gene model | | |
|---|---|---|---|---|
| | | Bladder cancer | Non-bladder cancer | Sum |
| Pathological diagnosis | Bladder cancer | 58 | 5 | 63 |
| | Non-bladder cancer | 4 | 40 | 44 |
| Sum | | 62 | 45 | 107 |

TABLE 3

Identification results of 32-gene model in 106 sample from validation set

| Validation set 2 | | Identification results of 32-gene model | | |
|---|---|---|---|---|
| | | Bladder cancer | Non-bladder cancer | Sum |
| Pathological diagnosis | bladder cancer | 68 | 6 | 74 |
| | non-bladder cancer | 1 | 31 | 32 |
| Sum | | 69 | 37 | 106 |

The primer sets of 32 genes were designed separately as below:

CA9 gene: the forward primer is as set forth in SEQ ID NO: 1, and the reverse primer is as set forth in SEQ ID NO: 2;

CDK1 gene: the forward primer is as set forth in SEQ ID NO: 3, and the reverse primer is as set forth in SEQ ID NO: 4;

CTSE gene: the forward primer is as set forth in SEQ ID NO: 5, and the reverse primer is as set forth in SEQ ID NO: 6;

DMBT1 gene: the forward primer is as set forth in SEQ ID NO: 7, and the reverse primer is as set forth in SEQ ID NO: 8;

ERBB2 gene: the forward primer is as set forth in SEQ ID NO: 9, and the reverse primer is as set forth in SEQ ID NO: 10;

HOXA13 gene: the forward primer is as set forth in SEQ ID NO: 11, and the reverse primer is as set forth in SEQ ID NO: 12;

IGF2 gene: the forward primer is as set forth in SEQ ID NO: 13, and the reverse primer is as set forth in SEQ ID NO: 14;

CXCR2 gene: the forward primer is as set forth in SEQ ID NO: 15, and the reverse primer is as set forth in SEQ ID NO: 16;

MAGEA3 gene: the forward primer is as set forth in SEQ ID NO: 17, and the reverse primer is as set forth in SEQ ID NO: 18;

MDK gene: the forward primer is as set forth in SEQ ID NO: 19, and the reverse primer is as set forth in SEQ ID NO: 20;

MMP1 gene: the forward primer is as set forth in SEQ ID NO: 21, and the reverse primer is as set forth in SEQ ID NO: 22;

MMP12 gene: the forward primer is as set forth in SEQ ID NO: 23, and the reverse primer is as set forth in SEQ ID No. 24;

RBP2 gene: the forward primer is as set forth in SEQ ID NO: 25, and the reverse primer is as set forth in SEQ ID NO: 26;

CCL18 gene: the forward primer is as set forth in SEQ ID NO: 27, and the reverse primer is as set forth in SEQ ID NO: 28;

SNAI2 gene: the forward primer is as set forth in SEQ ID NO: 29, and the reverse primer is as set forth in SEQ ID NO: 30;

VEGFA gene: the forward primer is as set forth in SEQ ID NO: 31, and the reverse primer is as set forth in SEQ ID NO: 32;

MFAP5 gene: the forward primer is as set forth in SEQ ID NO: 33, and the reverse primer is as set forth in SEQ ID NO: 34;

SGK2 gene: the forward primer is as set forth in SEQ ID NO: 35, and the reverse primer is as set forth in SEQ ID NO: 36;

WFDC2 gene: the forward primer is as set forth in SEQ ID NO: 37, and the reverse primer is as set forth in SEQ ID NO: 38;

POSTN gene: the forward primer is as set forth in SEQ ID NO: 39, and the reverse primer is as set forth in SEQ ID NO: 40;

NPFFR2 gene: the forward primer is as set forth in SEQ ID NO: 41, and the reverse primer is as set forth in SEQ ID NO: 42;

ANXA10 gene: the forward primer is as set forth in SEQ ID NO: 43, and the reverse primer is as set forth in SEQ ID NO: 44;

CTAG2 gene: the forward primer is as set forth in SEQ ID NO: 45, and the reverse primer is as set forth in SEQ ID NO: 46;

ZDHHC2 gene: the forward primer is as set forth in SEQ ID NO: 47, and the reverse primer is as set forth in SEQ ID NO: 48;

KRT20 gene: the forward primer is as set forth in SEQ ID NO: 49, and the reverse primer is as set forth in SEQ ID NO: 50;

PPP1R14D gene: the forward primer is as set forth in SEQ ID NO: 51, and the reverse primer is as set forth in SEQ ID NO: 52;

FGD3 gene: the forward primer is as set forth in SEQ ID NO: 53, and the reverse primer is as set forth in SEQ ID NO: 54;

AHNAK2 gene: the forward primer is as set forth in SEQ ID NO: 55, and the reverse primer is as set forth in SEQ ID NO: 56;

SEMA3D gene: the forward primer is as set forth in SEQ ID NO: 57, and the reverse primer is as set forth in SEQ ID NO: 58;

ZNF707 gene: the forward primer is as set forth in SEQ ID NO: 59, and the reverse primer is as set forth in SEQ ID NO: 60;

LOC100652931 gene: the forward primer is as set forth in SEQ ID NO: 61, and the reverse primer is as set forth in SEQ ID NO: 62;

LINC00565 gene: the forward primer is as set forth in SEQ ID NO: 63, and the reverse primer is as set forth in SEQ ID NO: 64.

The probe sequences of 32 genes are shown in Table 4:

TABLE 4

| No. | Genes | Probe Sequences |
| --- | --- | --- |
| 1 | CA9 | SEQ ID NO: 65 |
| 2 | CDK1 | SEQ ID NO: 66 |
| 3 | CTSE | SEQ ID NO: 67 |
| 4 | DMBT1 | SEQ ID NO: 68 |
| 5 | ERBB2 | SEQ ID NO: 69 |
| 6 | HOXA13 | SEQ ID NO: 70 |
| 7 | IGF2 | SEQ ID NO: 71 |
| 8 | CXCR2 | SEQ ID NO: 72 |
| 9 | MAGEA3 | SEQ ID NO: 73 |
| 10 | MDK | SEQ ID NO: 74 |
| 11 | MMP1 | SEQ ID NO: 75 |
| 12 | MMP12 | SEQ ID NO: 76 |
| 13 | RBP2 | SEQ ID NO: 77 |
| 14 | CCL18 | SEQ ID NO: 78 |
| 15 | SNAI2 | SEQ ID NO: 79 |
| 16 | VEGFA | SEQ ID NO: 80 |
| 17 | MFAP5 | SEQ ID NO: 81 |
| 18 | SGK2 | SEQ ID NO: 82 |
| 19 | WFDC2 | SEQ ID NO: 83 |
| 20 | POSTN | SEQ ID NO: 84 |
| 21 | NPFFR2 | SEQ ID NO: 85 |
| 22 | ANXA10 | SEQ ID NO: 86 |
| 23 | CTAG2 | SEQ ID NO: 87 |
| 24 | ZDHHC2 | SEQ ID NO: 88 |
| 25 | KRT20 | SEQ ID NO: 89 |
| 26 | PPP1R14D | SEQ ID NO: 90 |
| 27 | FGD3 | SEQ ID NO: 91 |
| 28 | AHNAK2 | SEQ ID NO: 92 |
| 29 | SEMA3D | SEQ ID NO: 93 |
| 30 | ZNF707 | SEQ ID NO: 94 |
| 31 | LOC100652931 | SEQ ID NO: 95 |
| 32 | LINC00565 | SEQ ID NO: 96 |

The results were shown in FIGURE. The Similarity Score for non-bladder cancer was 10, and that for bladder cancer was 90. The Similarity Scores of bladder cancer were the highest; therefore, the sample was identified as bladder cancer, which was consistent with the clinical diagnosis result.

Example 4

International patent application WO2014/118334 describes a method for bladder cancer detection based on the expression pattern of specific genes IGF2, MAGEA3, ANXA10, AHNAK2, CTSE, CRH, KLF9, KRT20, POSN, PPP1R14D, SLC1A6, TERT, ASAM, MCM10, EBF1, CFH, and MMP12 in urine samples. Although the method has shown high sensitivity (78.7%) and specificity (93.2%) in validation studies in western populations, further experiments are needed to confirm whether it is also applicable to Chinese populations. For the above 12 gene combinations, the inventors conducted the validation in 106 urine samples from Example 3. First, the desquamated cells in the urine are centrifuged, and then the total RNA is extracted by purification column extraction method; the cDNA was obtained by reverse transcription, and the expression level of 12 genes in the desquamated cells were detected by a real-time quantitative polymerase chain reaction; the Similarity Score between this sample and bladder cancer was calculated by the analysis model.

After comparing the identification results of each sample by the 12-gene model with clinical diagnosis results, the accuracy rate was 77.4%, sensitivity was 91.9%, and specificity was 43.8%, respectively, as shown in Table 5. It shows that comparing with the 12-gene model, the 32-gene model of the present invention has the same sensitivity (91.9% vs. 91.9%) and has a significant advantage in specificity (96.9% vs. 43.8%). The inventors further compared the 32 gene combinations with the 12 gene combinations and found that there were 8 overlapping genes: CTSE, KRT20, POSN, PPP1R14D, AHNAK2, ANXA10, IGF2, MAGEA3; 24 non-overlapping genes: WFDC2, CA9, CCL18, FGD3, MMP1, ERBB2, VEGFA, SEMA3D, NPFFR2, ZDHC2, ZNF707, RBP2, HOXA13, SGK2, MMP12, CTAG2, SNAI2, MFAP5, DMBT1, LINC00565, CDK1, MDK, CXCR2, LOC100652931. It is just because the inventors used the analysis technique of "big data and algorithm drive" to select the high specificity of bladder cancer gene combinations, creatively discovered and included the above 24 non-overlapping genes, the specificity was increased from 43.8% of the 12-gene to 96.9% of the 32-gene. Therefore, the 32 gene combinations have better clinical performance in Chinese patients with bladder cancer.

TABLE 5

Identifying results of 12-gene model in 106 cases from validation set

| Validation Set 2 | | Identification results of 12-gene model | | |
|---|---|---|---|---|
| | | Bladder cancer | Non-bladder cancer | Sum |
| Pathological diagnosis | Bladder cancer | 68 | 6 | 74 |
| | Non-bladder cancer | 18 | 14 | 32 |
| Sum | | 86 | 20 | 106 |

The above examples only express the mode of implementation of the present invention, and the description is relatively specific and detailed, but it shall not be construed as a limitation of the scope of the present invention. It should be noted that, for ordinary technicians in the field, a number of variations and improvements may be made without deviating from the conception of the present invention, which are within the protection scope of the present invention. Therefore, the protection scope of the present invention shall be subject to the attached claims.

We claim:

1. A gene chip for a diagnosis, prognosis, or monitoring of bladder cancer, wherein the gene chip comprises:
a solid phase carrier and a probe, wherein the probe is hybridized with sequences of 32 genes to be tested and/or complementary sequences of the 32 genes, wherein the probe is as set forth in SEQ ID NO: 65-SEQ ID NO: 96, respectively, wherein a set of genes comprises the following 32 genes: CA9 gene, CDK1 gene, CTSE gene, DMBT1 gene, ERBB2 gene, HOXA13 gene, IGF2 gene, CXCR2 gene, MAGEA3 gene, MDK gene, MMP1 gene, MMP12 gene, RBP2 gene, CCL18 gene, SNAI2 gene, VEGFA gene, MFAP5 gene, SGK2 gene, WFDC2 gene, POSTN gene, NPFFR2 gene, ANXA10 gene, CTAG2 gene, ZDHHC2 gene, KRT20 gene, PPP1R14D gene, FGD3 gene, AHNAK2 gene, SEMA3D gene, ZNF707 gene, LOC100652931 gene, and LINC00565 gene;
wherein the gene chip produces a result for bladder cancer detection.

2. A method of detecting bladder cancer using the gene chip according to claim 1, comprising the following steps:

1) obtaining a urine sample for the bladder cancer detection;
2) isolating total RNA from the urine sample;
3) placing the total RNA in contact with the gene chip;
4) determining expression levels of the 32 genes in the urine sample; and
5) diagnosing a presence of the bladder cancer based on statistical analysis of the expression levels.

3. A method of preparing the gene chip according to claim 1, comprising using a data-driven analysis method to select gene combinations with a specificity to the bladder cancer as the set of genes, wherein the data-driven analysis method comprises the following steps:
building a bladder cancer gene expression profile database, containing over 20,000 genes, 92 samples, and over 2 million data points;
correlating more than 20,000 human gene expression data in each of the 92 samples with clinical data of the 92 samples;

screening specific bladder cancer genes through a statistical analysis method T-test by analyzing a relevance of each of the specific bladder cancer genes to the bladder cancer;
extracting the specific bladder cancer genes with a highest correlation as signature genes, eventually obtaining the 32 genes for constructing a classifying model; and
establishing a statistical analysis model for the bladder cancer detection by using a Support Vector Machine, wherein for each sample to be tested, the statistical analysis model calculates a similarity score between a gene expression pattern of the sample to be tested and the bladder cancer in the bladder cancer gene expression profile database, and identifies whether the sample has the bladder cancer according to a principle of a highest similarity score.

4. The method according to claim 2, wherein the gene chip is arranged within a kit for the bladder cancer detection.

5. A kit for bladder cancer detection, wherein the kit comprises the gene chip according to claim 1, and biomarkers, wherein the biomarkers are the set of genes for the bladder cancer detection, wherein a result of the bladder cancer detection is bladder cancer positive or bladder cancer negative.

6. The kit according to claim 5, wherein the biomarkers are nucleic acids, oligonucleotide chains, or PCR primer sets.

7. The kit according to claim 6, wherein the biomarkers are PCR primer sets, wherein the PCR primer sets comprise:
PCR primers for the CA9 gene, comprising: a forward primer as set forth in SEQ ID NO: 1, and a reverse primer as set forth in SEQ ID NO: 2;
PCR primers for the CDK1 gene, comprising: a forward primer as set forth in SEQ ID NO: 3, and a reverse primer as set forth in SEQ ID NO: 4;
PCR primers for the CTSE gene, comprising: a forward primer as set forth in SEQ ID NO: 5, and a reverse primer as set forth in SEQ ID NO: 6;
PCR primers for the DMBT1 gene, comprising: a forward primer as set forth in SEQ ID NO: 7, and a reverse primer as set forth in SEQ ID NO: 8;
PCR primers for the ERBB2 gene, comprising: a forward primer as set forth in SEQ ID NO: 9, and a reverse primer as set forth in SEQ ID NO: 10;
PCR primers for the HOXA13 gene, comprising: a forward primer as set forth in SEQ ID NO: 11, and a reverse primer as set forth in SEQ ID NO: 12;
PCR primers for the IGF2 gene, comprising: a forward primer as set forth in SEQ ID NO: 13, and a reverse primer as set forth in SEQ ID NO: 14;
PCR primers for the CXCR2 gene, comprising: a forward primer as set forth in SEQ ID NO: 15, and a reverse primer as set forth in SEQ ID NO: 16;
PCR primers for the MAGEA3 gene, comprising: a forward primer as set forth in SEQ ID NO: 17, and a reverse primer as set forth in SEQ ID NO: 18;
PCR primers for the MDK gene, comprising: a forward primer as set forth in SEQ ID NO: 19, and a reverse primer as set forth in SEQ ID NO: 20;
PCR primers for the MMP1 gene, comprising: a forward pruner as set forth in SEQ ID NO: 21, and a reverse primer as set forth in SEQ ID NO: 22;
PCR primers for the MMP12 gene, comprising: a forward primer as set forth in SEQ ID NO: 23, and a reverse primer as set forth in SEQ ID NO: 24;
PCR primers for the RBP2 gene, comprising: a forward primer as set forth in SEQ ID NO: 25, and a reverse primer as set forth in SEQ ID NO: 26;
PCR primers for the CCL18 gene, comprising: a forward primer as set forth in SEQ ID NO: 27, and a reverse primer as set forth in SEQ ID NO: 28;
PCR primers for the SNAI2 gene, comprising: a forward pruner as set forth in SEQ ID NO: 29, and a reverse primer as set forth in SEQ ID NO: 30;
PCR primers for the VEGFA gene, comprising: a forward primer as set forth in SEQ ID NO: 31, and a reverse primer as set forth in SEQ ID NO: 32;
PCR primers for the MFAP5 gene, comprising: a forward primer as set forth in SEQ ID NO: 33, and a reverse primer as set forth in SEQ ID NO: 34;
PCR primers for the SGK2 gene, comprising: a forward primer as set forth in SEQ ID NO: 35, and a reverse primer as set forth in SEQ ID NO: 36;
PCR primers for the WFDC2 gene, comprising: a forward primer as set forth in SEQ ID NO: 37, and a reverse primer as set forth in SEQ ID NO: 38;
PCR primers for the POSTN gene, comprising: a forward primer as set forth in SEQ ID NO: 39, and a reverse primer as set forth in SEQ ID NO: 40;
PCR primers for the NPFFR2 gene, comprising: a forward primer as set forth in SEQ ID NO: 41, and a reverse primer as set forth in SEQ ID NO: 42;
PCR primers for the ANXA10 gene, comprising: a forward primer as set forth in SEQ ID NO: 43, and a reverse primer as set forth in SEQ ID NO: 44;
PCR primers for the CTAG2 gene, comprising: a forward primer as set forth in SEQ ID NO: 45, and a reverse primer as set forth in SEQ ID NO: 46;
PCR primers for the ZDHHC2 gene, comprising: a forward primer as set forth in SEQ ID NO: 47, and a reverse primer as set forth in SEQ ID NO: 48;
PCR primers for the KRT20 gene, comprising: a forward primer as set forth in SEQ ID NO: 49, and a reverse primer as set forth in SEQ ID NO: 50;
PCR primers for the PPP1R14D gene, comprising: a forward primer as set forth in SEQ ID NO: 51, and a reverse primer as set forth in SEQ ID NO: 52;
PCR primers for the FGD3 gene, comprising: a forward primer as set forth in SEQ ID NO: 53, and a reverse primer as set forth in SEQ ID NO: 54;
PCR primers for the AHNAK2 gene, comprising: a forward primer as set forth in SEQ ID NO: 55, and a reverse primer as set forth in SEQ ID NO: 56;
PCR primers for the SEMA3D gene, comprising: a forward primer as set forth in SEQ ID NO: 57, and a reverse primer as set forth in SEQ ID NO: 58;
PCR primers for the ZNF707 gene, comprising: a forward primer as set forth in SEQ ID NO: 59, and a reverse primer as set forth in SEQ ID NO: 60;
PCR primers for the LOC100652931 gene, comprising: a forward primer as set forth in SEQ ID NO: 61, and a reverse primer as set forth in SEQ ID NO: 62;
PCR primers for the LINC00565 gene, comprising: a forward primer as set forth in SEQ ID NO: 63, and a reverse primer as set forth in SEQ ID NO: 64.

8. A method of detecting bladder cancer using the kit according to claim 5, comprising:
1) obtaining a urine sample for the bladder cancer detection;
2) isolating total RNA from the urine sample;
3) placing the total RNA in contact with the biomarkers in the kit;

4) determining expression levels of the 32 genes in the urine sample; and
5) based on statistical analysis of the expression levels, performing a diagnosis, prognosis, or monitoring of the bladder cancer.

9. The method according to claim 2, wherein a result of the bladder cancer detection is bladder cancer positive or bladder cancer negative.

10. The method according to claim 2, wherein step 2 comprises the following steps: centrifuging desquamated cells in the urine sample, and then extracting the total RNA by a purification column extraction method using a purification column as a liquid elution medium.

11. The method according to claim 3, wherein the gene chip is arranged within a kit for the bladder cancer detection.

12. The method according to claim 8, wherein step 2 comprises the following steps: centrifuging desquamated cells in the urine sample, and then extracting the total RNA by a purification column extraction method using a purification column as a liquid elution medium.

13. A method of preparing the kit according to claim 5, comprising using a data-driven analysis method to select gene combinations with a specificity to the bladder cancer as the set of genes, wherein the data-driven analysis method comprises the following steps:
   building a bladder cancer gene expression profile database, containing over 20,000 genes, 92 samples, and over 2 million data points;
   correlating more than 20,000 human gene expression data in each of the 92 samples with clinical data of the 92 samples;
   screening specific bladder cancer genes through a statistical analysis method T-test by analyzing a relevance of each of the specific bladder cancer genes to the bladder cancer,
   extracting the specific bladder cancer genes with a highest correlation as signature genes, eventually obtaining the 32 genes for constructing a classifying model; and
   establishing a statistical analysis model for the bladder cancer detection by using a Support Vector Machine, wherein for each sample to be tested, the statistical analysis model calculates a similarity score between a gene expression pattern of the sample to be tested and the bladder cancer in the bladder cancer gene expression profile database, and identifies whether the sample has the bladder cancer according to a principle of a highest similarity score.

14. The method according to claim 8, wherein the biomarkers are nucleic acids, oligonucleotide chains, or PCR primer sets.

15. The kit according to claim 14, wherein the biomarkers are PCR primer sets, wherein the PCR primer sets comprise:
   PCR primers for the CA9 gene, comprising: a forward primer as set forth in SEQ ID NO: 1, and a reverse primer as set forth in SEQ ID NO: 2;
   PCR primers for the CDK1 gene, comprising: a forward primer as set forth in SEQ ID NO: 3, and a reverse primer as set forth in SEQ ID NO: 4;
   PCR primers for the CTSE gene, comprising: a forward primer as set forth in SEQ ID NO: 5, and a reverse primer as set forth in SEQ ID NO: 6;
   PCR primers for the DMBT1 gene, comprising: a forward primer as set forth in SEQ ID NO: 7, and a reverse primer as set forth in SEQ ID NO: 8;
   PCR primers for the ERBB2 gene, comprising: a forward primer as set forth in SEQ ID NO: 9, and a reverse primer as set forth in SEQ ID NO: 10;
   PCR primers for the HOXA13 gene, comprising: a forward primer as set forth in SEQ ID NO: 11, and a reverse primer as set forth in SEQ ID NO: 12;
   PCR primers for the IGF2 gene, comprising: a forward primer as set forth in SEQ ID NO: 13, and a reverse primer as set forth in SEQ ID NO: 14;
   PCR primers for the CXCR2 gene, comprising: a forward primer as set forth in SEQ ID NO: 15, and a reverse primer as set forth in SEQ ID NO: 16;
   PCR primers for the MAGEA3 gene, comprising: a forward primer as set forth in SEQ ID NO: 17, and a reverse primer as set forth in SEQ ID NO: 18;
   PCR primers for the MDK gene, comprising: a forward primer as set forth in SEQ ID NO: 19, and a reverse primer as set forth in SEQ ID NO: 20;
   PCR primers for the MMP1 gene, comprising: a forward pruner as set forth in SEQ ID NO: 21, and a reverse primer as set forth in SEQ ID NO: 22;
   PCR primers for the MMP12 gene, comprising: a forward primer as set forth in SEQ ID NO: 23, and a reverse primer as set forth in SEQ ID NO: 24;
   PCR primers for the RBP2 gene, comprising: a forward primer as set forth in SEQ ID NO: 25, and a reverse primer as set forth in SEQ ID NO: 26;
   PCR primers for the CCL18 gene, comprising: a forward primer as set forth in SEQ ID NO: 27, and a reverse primer as set forth in SEQ ID NO: 28;
   PCR primers for the SNAI2 gene, comprising: a forward pruner as set forth in SEQ ID NO: 29, and a reverse primer as set forth in SEQ ID NO: 30;
   PCR primers for the VEGFA gene, comprising: a forward primer as set forth in SEQ ID NO: 31, and a reverse primer as set forth in SEQ ID NO: 32,
   PCR primers for the MFAP5 gene, comprising: a forward primer as set forth in SEQ ID NO: 33, and a reverse primer as set forth in SEQ ID NO: 34;
   PCR primers for the SGK2 gene, comprising: a forward primer as set forth in SEQ ID NO: 35, and a reverse primer as set forth in SEQ ID NO: 36;
   PCR primers for the WFDC2 gene, comprising: a forward primer as set forth in SEQ ID NO: 37, and a reverse primer as set forth in SEQ ID NO: 38;
   PCR primers for the POSTN gene, comprising: a forward primer as set forth in SEQ ID NO: 39, and a reverse primer as set forth in SEQ ID NO: 40;
   PCR primers for the NPFFR2 gene, comprising: a forward primer as set forth in SEQ ID NO: 41, and a reverse primer as set forth in SEQ ID NO: 42;
   PCR primers for the ANXA10 gene, comprising: a forward primer as set forth in SEQ ID NO: 43, and a reverse primer as set forth in SEQ ID NO: 44;
   PCR primers for the CTAG2 gene, comprising: a forward primer as set forth in SEQ ID NO: 45, and a reverse primer as set forth in SEQ ID NO: 46;
   PCR primers for the ZDHHC2 gene, comprising: a forward primer as set forth in SEQ ID NO: 47, and a reverse primer as set forth in SEQ ID NO: 48;
   PCR primers for the KRT20 gene, comprising: a forward primer as set forth in SEQ ID NO: 49, and a reverse primer as set forth in SEQ ID NO: 50;
   PCR primers for the PPP1R14D gene, comprising: a forward primer as set forth in SEQ ID NO: 51, and a reverse primer as set forth in SEQ ID NO: 52;
   PCR primers for the FGD3 gene, comprising: a forward primer as set forth in SEQ ID NO: 53, and a reverse primer as set forth in SEQ ID NO: 54;

PCR primers for the AHNAK2 gene, comprising: a forward primer as set forth in SEQ ID NO: 55, and a reverse primer as set forth in SEQ ID NO: 56;

PCR primers for the SEMA3D gene, comprising: a forward primer as set forth in SEQ ID NO: 57, and a reverse primer as set forth in SEQ ID NO: 58;

PCR primers for the ZNF707 gene, comprising: a forward primer as set forth in SEQ ID NO: 59, and a reverse primer as set forth in SEQ ID NO: 60;

PCR primers for the LOC100652931 gene, comprising: a forward primer as set forth in SEQ ID NO: 61, and a reverse primer as set forth in SEQ ID NO: 62;

PCR primers for the LINC00565 gene, comprising: a forward primer as set forth in SEQ ID NO: 63, and a reverse primer as set forth in SEQ ID NO: 64.

* * * * *

SEQUENCE LISTING

```
<160> NUMBER OF SEQ ID NOS: 96

<210> SEQ ID NO 1
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 1
tcagccgcta cttccaatat g                                             21

<210> SEQ ID NO 2
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 2
```
ttagcactca gcatcactgt c                                            21

<210> SEQ ID NO 3
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 3
ggtcaagtgg tagccatgaa                                              20

<210> SEQ ID NO 4
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 4
gcacatcctg aagactgact at                                           22

<210> SEQ ID NO 5
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 5
gctacgacca ctcccatttc                                              20

<210> SEQ ID NO 6
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 6
ggcacactcc acagcatatt a                                            21

<210> SEQ ID NO 7
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 7
tggttctccc acaactgtaa tc                                           22

<210> SEQ ID NO 8

```
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 8
ggacgggtga tgttgagaaa                                            20

<210> SEQ ID NO 9
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 9
gagacagagt accatgcaga tg                                         22

<210> SEQ ID NO 10
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 10
ccacacagtc acaccataac t                                          21

<210> SEQ ID NO 11
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 11
cgggaatacg ccacgaataa                                            20

<210> SEQ ID NO 12
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 12
cctgttctgg aaccagattg t                                          21

<210> SEQ ID NO 13
<211> LENGTH: 22
<212> TYPE: DNA
<213> ORGANISM: Artificial Sequence
<220> FEATURE:
```

```
<223> OTHER INFORMATION: the sequence is synthetized
<220> FEATURE:
<221> NAME/KEY: misc_feature
<223> OTHER INFORMATION: Primers

<400> SEQUENCE: 13
cactctgtct ctcccactat ct                                              22

<210> SEQ ID NO 14
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 14
cgggccagat gttgtacttt                                                 20

<210> SEQ ID NO 15
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 15
ctcgtgatgc tggtcatctt at                                              22

<210> SEQ ID NO 16
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 16
caaggtcagg gcaaagagta g                                               21

<210> SEQ ID NO 17
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 17
gactccagca accaagaaga                                                 20

<210> SEQ ID NO 18
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers
```

<400> SEQUENCE: 18
ctcgatactt gaggagcaga aa                                    22

<210> SEQ ID NO 19
<211> LENGTH: 18
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 19
aagaaggcgc gctacaat                                         18

<210> SEQ ID NO 20
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 20
gtcctttccc ttccctttct t                                     21

<210> SEQ ID NO 21
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 21
ctctgacatt caccaaggtc tc                                    22

<210> SEQ ID NO 22
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 22
gatttcctcc aggtccatca aa                                    22

<210> SEQ ID NO 23
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 23
ctgtcactac cgtgggaaat aa                                    22

<210> SEQ ID NO 24
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 24
aggttggcca taaggaagaa a                                              21

<210> SEQ ID NO 25
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 25
acctgggaga tggagagtaa t                                              21

<210> SEQ ID NO 26
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 26
gagtgagacg tactgcaatc tt                                             22

<210> SEQ ID NO 27
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 27
gtgtcatcct cctaaccaag ag                                             22

<210> SEQ ID NO 28
<211> LENGTH: 19
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 28
cctcaggcat tcagcttca                                                 19

<210> SEQ ID NO 29
<211> LENGTH: 22

```
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 29
ctctctcctc tttccggata ct                                              22

<210> SEQ ID NO 30
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 30
gcttggactg tagtctttcc tc                                              22

<210> SEQ ID NO 31
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 31
tggtgtcttc actggatgta ttt                                             23

<210> SEQ ID NO 32
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 32
agtctctcat ctcctcctct tc                                              22

<210> SEQ ID NO 33
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 33
gaatgatccc gctacagatg aa                                              22

<210> SEQ ID NO 34
<211> LENGTH: 21
<212> TYPE: DNA
<213> ORGANISM: Artificial Sequence
<220> FEATURE:
<223> OTHER INFORMATION: the sequence is synthetized
```

```
<220> FEATURE:
<221> NAME/KEY: misc_feature
<223> OTHER INFORMATION: Primers

<400> SEQUENCE: 34
gtagagcctt gtgcaggtaa a                                              21

<210> SEQ ID NO 35
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 35
gtcatcggca aagggaacta                                                20

<210> SEQ ID NO 36
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 36
gatgtggctc tgctctttct                                                20

<210> SEQ ID NO 37
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 37
tgctctctgc ccaatgataa g                                              21

<210> SEQ ID NO 38
<211> LENGTH: 18
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 38
caccttccca cagccatt                                                  18

<210> SEQ ID NO 39
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers
```

```
<400> SEQUENCE: 39
gagctttaca acgggcaaat ac                                              22

<210> SEQ ID NO 40
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 40
ctcccttgct tactcccttt c                                               21

<210> SEQ ID NO 41
<211> LENGTH: 19
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 41
tcacacaggc aggaagaac                                                  19

<210> SEQ ID NO 42
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 42
gggcagccat gagagaataa                                                 20

<210> SEQ ID NO 43
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 43
tcttcccagc tcccaatttc                                                 20

<210> SEQ ID NO 44
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 44
ctggtatgcc tctgcaatca                                                 20
```

```
<210> SEQ ID NO 45
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 45
tccggcaacc tactgtttat g                                              21

<210> SEQ ID NO 46
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 46
accttgtgtt tgggtgttct                                                20

<210> SEQ ID NO 47
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 47
agagagagcc aagaggagaa g                                              21

<210> SEQ ID NO 48
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 48
tccagacatg gtcctggtat ag                                             22

<210> SEQ ID NO 49
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 49
agagctgcga agtcagatta ag                                             22

<210> SEQ ID NO 50
<211> LENGTH: 22
<212> TYPE: DNA
```

```
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 50
ggagatcagc ttccactgtt ag                                              22

<210> SEQ ID NO 51
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 51
ccttgcccag accaatactt                                                 20

<210> SEQ ID NO 52
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 52
ggaccttctt acatgggttc tc                                              22

<210> SEQ ID NO 53
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 53
tgatcaagga gggccaaatc                                                 20

<210> SEQ ID NO 54
<211> LENGTH: 19
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 54
agcttgggca cacagtaaa                                                  19

<210> SEQ ID NO 55
<211> LENGTH: 20
<212> TYPE: DNA
<213> ORGANISM: Artificial Sequence
<220> FEATURE:
<223> OTHER INFORMATION: the sequence is synthetized
<220> FEATURE:
```

```
<221> NAME/KEY: misc_feature
<223> OTHER INFORMATION: Primers

<400> SEQUENCE: 55
cagatgccta aggtgggttt                                              20

<210> SEQ ID NO 56
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 56
tcctcacagg gagagagaat ag                                           22

<210> SEQ ID NO 57
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 57
gcggcactct gtgatgtata a                                            21

<210> SEQ ID NO 58
<211> LENGTH: 25
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 58
ccactatctg tgtcagtctg taatc                                        25

<210> SEQ ID NO 59
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 59
ccaagagacc ttgtgatcat cc                                           22

<210> SEQ ID NO 60
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 60
```
gcctgaagcc cttcctaaag                                              20

<210> SEQ ID NO 61
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 61
ctccttctgc tgtggtaaga ag                                           22

<210> SEQ ID NO 62
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 62
tctacgtgta ggacctccat aat                                          23

<210> SEQ ID NO 63
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 63
gacccagcac aggattagaa a                                            21

<210> SEQ ID NO 64
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 64
gctgacatgg agaaggattg a                                            21

<210> SEQ ID NO 65
<211> LENGTH: 25
<212> TYPE: DNA
<213> ORGANISM: Artificial Sequence
<220> FEATURE:
<223> OTHER INFORMATION: the sequence is synthetized

<400> SEQUENCE: 65
ccagggtgtc atctggactg tgttt                                        25

<210> SEQ ID NO 66
<211> LENGTH: 26
<212> TYPE: DNA

```
<213> ORGANISM: Artificial Sequence
<220> FEATURE:
<223> OTHER INFORMATION: the sequence is synthetized

<400> SEQUENCE: 66
ttcccgaatt gcagtactag gaaccc                                          26

<210> SEQ ID NO 67
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 67
agcttactgg cagattgcac tgga                                            24

<210> SEQ ID NO 68
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 68
tgctggtgtc atctgctcag gaaa                                            24

<210> SEQ ID NO 69
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 69
acacatcact ctggtgggtg aacc                                            24

<210> SEQ ID NO 70
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 70
actaaggaca aacggaggcg gat                                             23

<210> SEQ ID NO 71
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 71
acaacagctg acctcatttc ccga                                            24

<210> SEQ ID NO 72
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 72
ctacctgctg aacctagcct tggc                                            24
```

<210> SEQ ID NO 73
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 73
agtgctgctt ggaactcgga ctc                                    23

<210> SEQ ID NO 74
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 74
cccaagacca agcaaaggc caaa                                    24

<210> SEQ ID NO 75
<211> LENGTH: 25
<212> TYPE: DNA
<213> ORGANISM: Artificial Sequence
<220> FEATURE:
<223> OTHER INFORMATION: the sequence is synthetized

<400> SEQUENCE: 75
aggagagttg tcccgatgat ctccc                                  25

<210> SEQ ID NO 76
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 76
agacaggttc ttctggctga aggt                                   24

<210> SEQ ID NO 77
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 77
actttgaggg ctacatgaag gccc                                   24

<210> SEQ ID NO 78
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 78
agtgggtcca gaaatacatc agcgac                                 26

<210> SEQ ID NO 79
<211> LENGTH: 24
<212> TYPE: DNA
<213> ORGANISM: Artificial Sequence(unknown)
<220> FEATURE:

<223> OTHER INFORMATION: the sequence is synthetized

<400> SEQUENCE: 79
tcctccatct gacacctcct ccaa                                          24

<210> SEQ ID NO 80
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 80
actgctgtgg acttgagttg ggag                                          24

<210> SEQ ID NO 81
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 81
cacagatgac ttggagtgct ggga                                          24

<210> SEQ ID NO 82
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 82
tactggccaa gcgcaagtct gat                                           23

<210> SEQ ID NO 83
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 83
agtgtcctgg ccagatgaaa tgct                                          24

<210> SEQ ID NO 84
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 84
catcggaggc aaacagctca gagt                                          24

<210> SEQ ID NO 85
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 85
aagatgctcc tgattgtggc cct                                           23

-continued

```
<210> SEQ ID NO 86
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 86
atggatgccc aaatgctagg agga                                              24

<210> SEQ ID NO 87
<211> LENGTH: 22
<212> TYPE: DNA
<213> ORGANISM: Artificial Sequence
<220> FEATURE:
<223> OTHER INFORMATION: the sequence is synthetized

<400> SEQUENCE: 87
agttcgggac caggacaggg aa                                                22

<210> SEQ ID NO 88
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 88
cttaggcgag cagccaagga tctt                                              24

<210> SEQ ID NO 89
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 89
tgctaaactg gctgctgagg actt                                              24

<210> SEQ ID NO 90
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 90
catgctgtct tcaagccctg cttc                                              24

<210> SEQ ID NO 91
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 91
ttgaacagga agaggtggcg gtc                                               23

<210> SEQ ID NO 92
<211> LENGTH: 24
<212> TYPE: DNA
<213> ORGANISM: Artificial Sequence
<220> FEATURE:
<223> OTHER INFORMATION: the sequence is synthetized
```

```
<400> SEQUENCE: 92
catcccggct tgatctcact ggtc                                          24

<210> SEQ ID NO 93
<211> LENGTH: 0
<212> TYPE: DNA
<213> ORGANISM: Artificial Sequence
<220> FEATURE:
<223> OTHER INFORMATION: ttgcaggagg accaacgttc aaga

<400> SEQUENCE: 93

000

<210> SEQ ID NO 94
<211> LENGTH: 24
<212> TYPE: DNA
<213> ORGANISM: Artificial Sequence(unknown)
<220> FEATURE:
<223> OTHER INFORMATION: the sequence is synthetized

<400> SEQUENCE: 94
agaaagagcc agggaaggaa gcag                                          24

<210> SEQ ID NO 95
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 95
aattggatga gaggccaagg tccc                                          24

<210> SEQ ID NO 96
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 96
tagcatgaca aggcagcact cagg                                          24
```